United States Patent [19]
Wortrich

[11] Patent Number: 5,458,608
[45] Date of Patent: Oct. 17, 1995

[54] LAPAROSCOPIC INSTRUMENTS AND METHODS

[75] Inventor: Theodore S. Wortrich, Long Beach, Calif.

[73] Assignee: Surgin Surgical Instrumentation Inc., Tustin, Calif.

[21] Appl. No.: 72,133

[22] Filed: Jun. 3, 1993

[51] Int. Cl.$^6$ ................................................ A61B 17/00
[52] U.S. Cl. .................... 606/139; 606/60; 606/72; 606/213; 606/232; 227/110; 227/147; 227/148
[58] Field of Search ................... 606/60, 67, 72, 606/75, 99, 100, 104, 139, 213, 232; 227/110, 142, 144, 147, 148; 81/124.2, 176.1, 177.8, 177.9

[56] References Cited

U.S. PATENT DOCUMENTS

| | | | |
|---|---|---|---|
| 207,315 | 8/1878 | Stack | 227/147 |
| 2,430,532 | 11/1947 | Rayburn | 227/142 |
| 4,712,550 | 12/1987 | Sinnet . | |
| 4,784,138 | 11/1988 | Sinnet . | |
| 4,838,471 | 6/1989 | Chiesa | 227/147 |
| 4,884,572 | 12/1989 | Bays et al. | 606/139 |
| 4,895,148 | 1/1990 | Bays et al. . | |
| 5,059,206 | 10/1991 | Winters | 606/213 |
| 5,071,420 | 12/1991 | Paulos et al. | 606/104 |
| 5,275,151 | 1/1994 | Shockey et al. | 128/4 |
| 5,328,077 | 7/1994 | Lou | 606/75 |

FOREIGN PATENT DOCUMENTS

| | | | |
|---|---|---|---|
| 1653750 | 6/1991 | U.S.S.R. | 606/104 |

OTHER PUBLICATIONS

S. Nivatvongs, M.D. and D. T. Fang, M.D., "The Use of Thumbtacks to Stop Massive Presacral Herorrhage," *Dis. Col. & Rect.* (Sep., 1986), pp. 589–590.

W. Qunyao, M.D., S. Weijin, M.D., Z. Youren. M.D., Z. Wenqing, M.D. and H. Zhengrui, "New Concepts in Severe Presacral Hemorrhage During Proctectomy," *Arch. Surg.* (1985), vol. 120, pp. 1013–1020.

"Sutureless Laparoscopic Rectopexy For Procidentia, " Irwin R. Berman, *Dis Colon Rectum*, Jul. 1992, pp. 689–693.

*Primary Examiner*—Stephen C. Pellegrino
*Assistant Examiner*—Jeffrey A. Schmidt
*Attorney, Agent, or Firm*—Merchant, Gould, Smith, Edell, Welter and Schmidt

[57] ABSTRACT

A tacker instrument for laparoscopic applications fits within a cannula and incorporates within a sleeve a positioning and driving system coupled to a tack holder mechanism at the distal end. The tack is held unexposed during entry but then may be extended to a predetermined position for embedment, with position being verifiable through the sleeve. Impact forces for embedding or removing the tack are applied to the positioning and driving mechanism, and the tack and tack holder are configured so that there is lateral disengagement or engagement of the two. In one version the mechanism is linear, while in a second version the distal end of the sleeve device can be angulated for perpendicular tack entry or removal with impelling forces being applied through a flexible shaft segment.

28 Claims, 8 Drawing Sheets

LAPAROSCOPIC INSTRUMENTS AND METHODS

BACKGROUND OF THE INVENTION

This invention relates to devices and methods for laparoscopic surgery, and more particularly to devices and methods for inserting and removing tacks during laparoscopic surgery.

Laparoscopic surgery, or the effecting of surgical procedures in body cavities through body walls, became feasible with the development of small cross-section viewing and manipulating instruments, and has since been the procedure of choice for a number of particular operative situations. Consequently, there have been developed a significant number of devices that can be inserted into a body cavity for moving, cutting, fastening and cauterizing, among other functions, so that laparoscopic procedures can be carried out quickly, with low trauma and thus with minimal discomfort and recovery time.

A number of different surgical procedures have been developed or are contemplated for use, for example, in the abdominal cavity. Abdominal rectopexy, involving such conditions as a prolapsed uterus, prolapsed vagina or prolapsed rectum, has been treated using this approach. The abdominal cavity affords not only sufficient volume in which to conduct necessary surgical procedures, while visualizing the site through a camera port or using an endoscope, but also includes usable anchor structures, such as cartilage of the sacrum. Experimental procedures have shown that prolapsed tissue can be manipulated to, and then anchored in, a given position, using a mesh of sterile, inert filaments. For this purpose, however, a laparoscopic tacking instrument is needed that will meet the size and shape constraints imposed on any laparoscopic device. The instrument should further maintain a tack in unexposed position during insertion, provide a seating surface that does not slip when the tack is being driven in, allow verification of the tack position, retain the tack securely so that it cannot become loose within the body cavity, and permit application of the necessary forces for driving the tack into and out of position. Both embedment and disengagement of the tack should be feasible with the same instrument.

SUMMARY OF THE INVENTION

A laparoscopic tacking instrument and method in accordance with the invention incorporates a sleeve that is sufficiently thin to fit within a cannula and long enough to extend proximate to a tacking site inside a body cavity at its distal end. The instrument includes an exterior portion accessible to a surgeon, together with a driving and positioning shaft extending through the sleeve and having a tack holding device mounted in its distal end. Also, in the exterior portion, a positioner is incorporated that is configured to enable control of both axial and circumferential positions of the shaft and the tack relative to the sleeve.

The positioner may include a shaped continuous guide slot in a positioning sleeve attached to the proximal and of the sleeve body, and an interior positioning pin coupled to the shaft rod. This arrangement facilitates entry of the sleeve into the body cavity with the tack securely held in the tack holder but not exposed. Thereafter, the sleeve and tack may be placed in position at a given region and driven in to the sacrum until fully seated. The tack holder may then be slid sideways from the tack to complete the procedure. A tack, once embedded, may be removed by a reverse procedure.

Among the features employed with this system are a viewing window in the sleeve through which the position of the tack positioning mechanism and therefore the tack, may be verified. Also, a slidable weight may be attached to the proximal end of the positioning and driving shaft to provide adequate impact force without vigorous motion.

In a specific example of the laparoscopic instrument, the cylindrical sleeve is arranged for direct insertion through a cannula or port. Spaced apart from the distal end of the sleeve is a viewing guide slot, with indicia which enable the operator to see ("visualize") the drive mechanism and its position relative to the sleeve. The tack holder comprises a pair of laterally extending arms which fit a groove between two spaced apart heads in the tack, the arms being biased under spring pressure toward the distal end of the drive mechanism, so that the tack is held firmly in position but can nonetheless be released when it should be disengaged. A control knob on the drive mechanism exterior to the body wall is accessible to the surgeon for controlling sleeve and tack position. A weighted mass or impeller is attachable to the outer end of the drive mechanism, and is freely reciprocable over a short distance so that the mass of the impeller enables the tack to be driven into or out of position with a series of controllable impacts requiring little strength or exertion.

In accordance with a different feature of the invention, the sleeve and internal drive rod mechanism are arranged to enable the distal end of the instrument to be pivoted through a limited angle, while still providing the positioning, driving and disengagement functions. This arrangement facilitates entering the tack into, or removing the tack from, the sacrum in a perpendicular direction where the attitude of the sacrum relative to the point of eating through the body wall is somewhat off line. In a specific example, the sleeve mechanism has a rotatable principal body about an interior fixed tube which supports an end tube segment encompassing the tack holder and tack during insertion. The end tube segment is pivotable about its proximal end on the interior fixed tube as the principal body of the sleeve mechanism is turned. A drive and positioning mechanism extends through the pivoting means and includes a flexible shaft portion of sufficient axial rigidity to transfer impact forces without buckling to the tack holder as the impeller is used. Means are provided for selecting the tack position, and visualizing it as well, through a viewing window in the end tube segment.

Other aspects of the invention facilitate use of systems and method in accordance with the invention for special purposes or functions. The tack itself advantageously has a double head in which the uppermost or proximal head is of smaller diameter than the other of the pair. Further, the upper head may include two or more diametrally opposed peripheral notches, such that a suture filament can be wrapped around the groove between the two heads and brought out through the notches. Thus, the tack itself can be used as a post when manipulating organs or elements, or as an anchor for tying off sutures. Another aspect is that the tack holding part of the instrument can be configured, together with the distal end of the driving and positioning mechanism, as a replaceable cartridge. For embedment of more than one tack, or a change of tack size, valuable time can be saved by rapid interchange of pre-loaded cartridges.

Another variation within the scope of the invention lies in the employment of pneumatic devices. For example, a pneumatic impulser may be attached to the proximal end of the positioning and driving mechanism. The pneumatic impulser is sufficiently small and light to be left in position during initial steps of a procedure, and can be remotely controlled as by a foot pedal. Such a mechanism can substantially shorten the time needed for tack embedment or removal.

BRIEF DESCRIPTION OF THE DRAWINGS

A better understanding of the invention may be had by reference to the following drawings, taken in conjunction with the accompanying description, in which like reference numbers refer to like parts and in which.

DETAILED DESCRIPTION OF THE INVENTION

Figure 1:
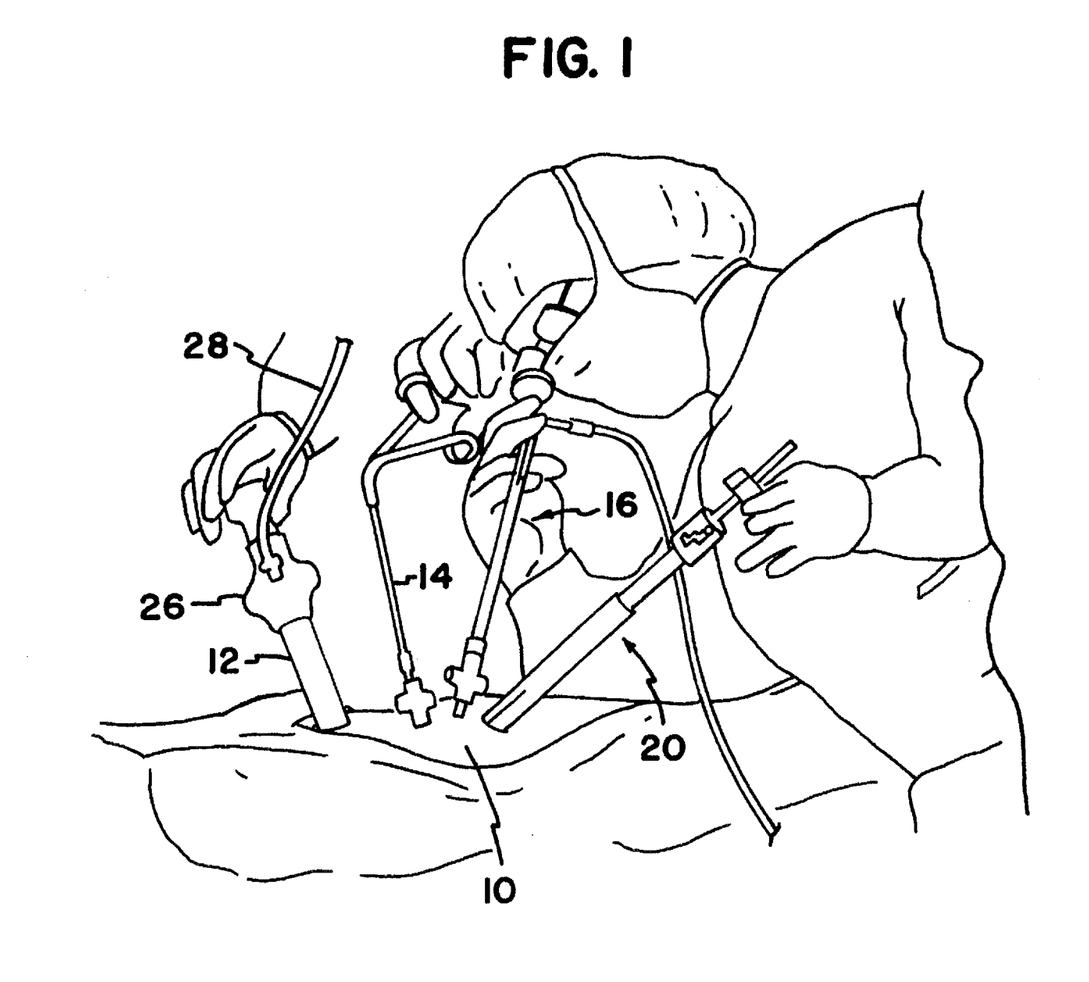
FIG. 1 is a generalized representation of an operative scene during a laparoscopic procedure using a laparoscopic instrument in accordance with the invention.
Figure 2:
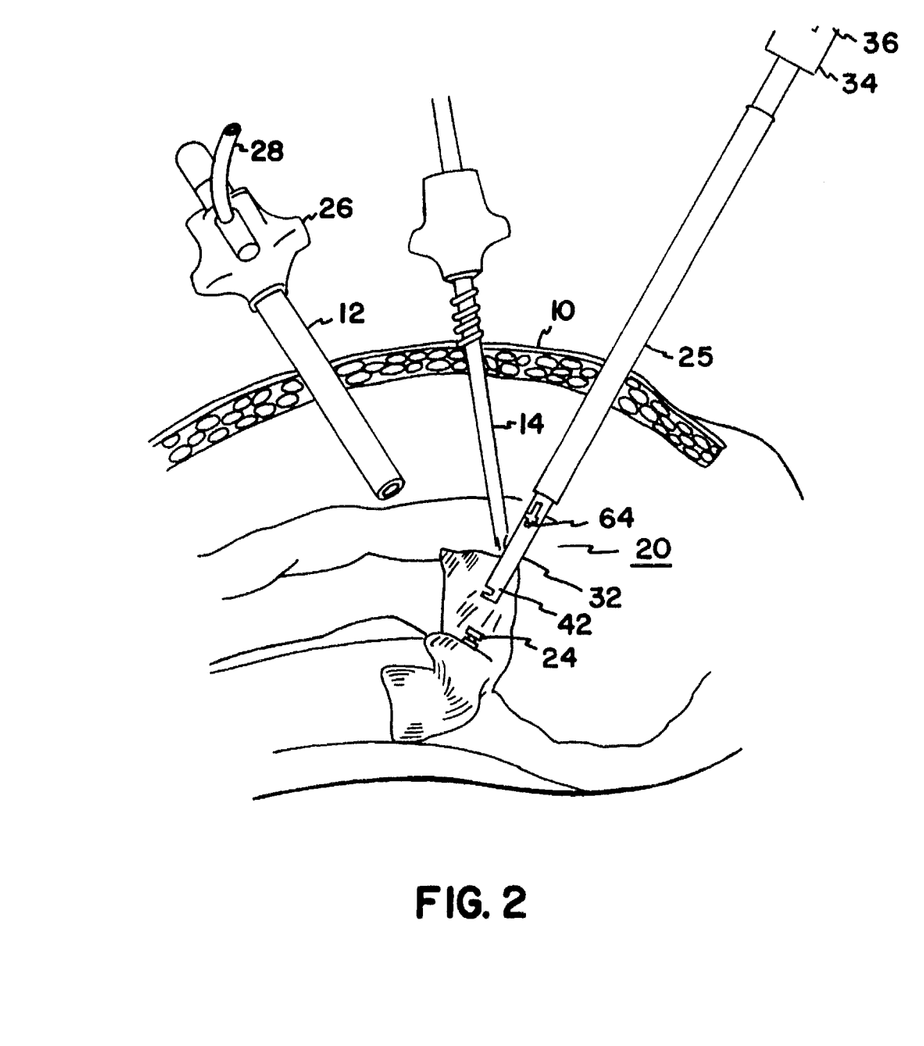
FIG. 2 is a combined sectional and perspective view of an operative site, during a laparoscopic procedure in accordance with the invention.
Figure 3:
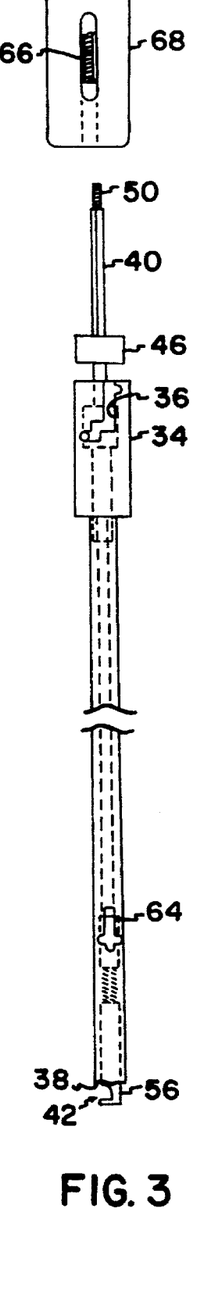
FIG. 3 is a side view in partially exploded form of a laparoscopic instrument in accordance with the invention.
Figure 4:
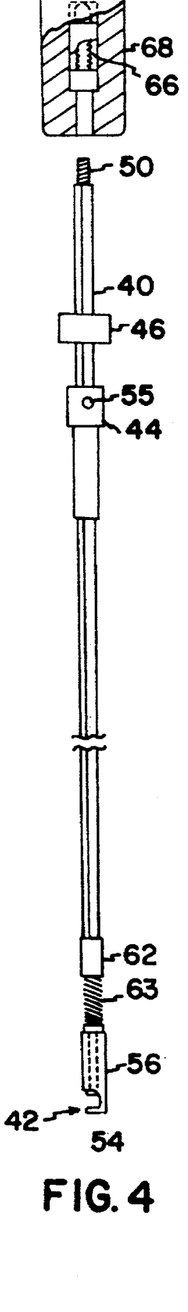
FIG. 4 is a side view of a positioning and driving mechanism used in the instrument of FIG. 3.

Referring now to FIGS. 1 and 2, there is seen a generalized depiction of instruments and methodologies used in a typical laparoscopic procedure. After employing conventional insertion and insufflation procedures, a number of instruments have been positioned within a body cavity through the body wall 10. Illustrated are typical endoscope 12, a manipulator clamp 14, a viewer (seen in FIG. 1 only) and a laparoscopic instrument 20 in accordance with the invention. The surgeon is manipulating the laparoscopic instrument 20 at the same time he is observing the cavity interior through the viewer. A second surgeon manipulates the clamp 14, while viewing the image that is generated by the endoscope 12 on a separate video screen (not shown). In this particular procedure, the objective is to secure a prolapsed organ by attaching a synthetic biocompatible mesh 22 to interior cartilage, in this instance, the sacrum, using a surgical tack 24 as described in greater detail hereafter. The mesh 22 may be any of a number of materials approved for use in sterile, inert products for surgical applications. Laparoscopic operative procedures are based upon the fact that trauma to tissue is minimized while the interior of the cavity can visualized as fully as necessary utilizing the optical aids. Consequently all devices and instruments must have a small cross-sectional area at the body wall and within the body cavity. In the example of attachment of a prolapsed organ, the organ itself is secured to this biocompatible mesh 22 by staples or sutures (not shown).

In this example the laparoscopic instrument 20, referring now to FIGS. 1 to 6, is inserted through a cannula 25 extended into the body cavity after insufflation. An insufflation port 26 on the endoscope 12, or used at some other point where the pneumoperitoneum needle was previously used, is fed by a fluid pressure line 28, which typically injects air to prevent desufflation of the body cavity through leakage, so that internal organs remain readily accessible. The principal length of the instrument 20 itself is a cylindrical sleeve 32 which fits through the cannula 25 in sliding relation and which can be extended into proximity with the tacking site. As seen particularly in FIG. 5, the sleeve 32 includes a larger diameter positioning sleeve 34 at its proximal end, exterior to the body wall 10. The positioning sleeve 34 includes a position control slot 36 having axial and circumferential segments relative to the central axis of the instrument 20. Different positions along the position control slot 36 determine, as is described below, where a tack 24 held at the other end of the instrument 20 is located relative to the distal end of the sleeve 32. The terminal edge 38 at the distal end of the sleeve 32 has a periodic or serrated circumferential pattern, in this case, a generally sinusoidal variation, to provide better seating against a sacral area which it contacts.

Figure 5:
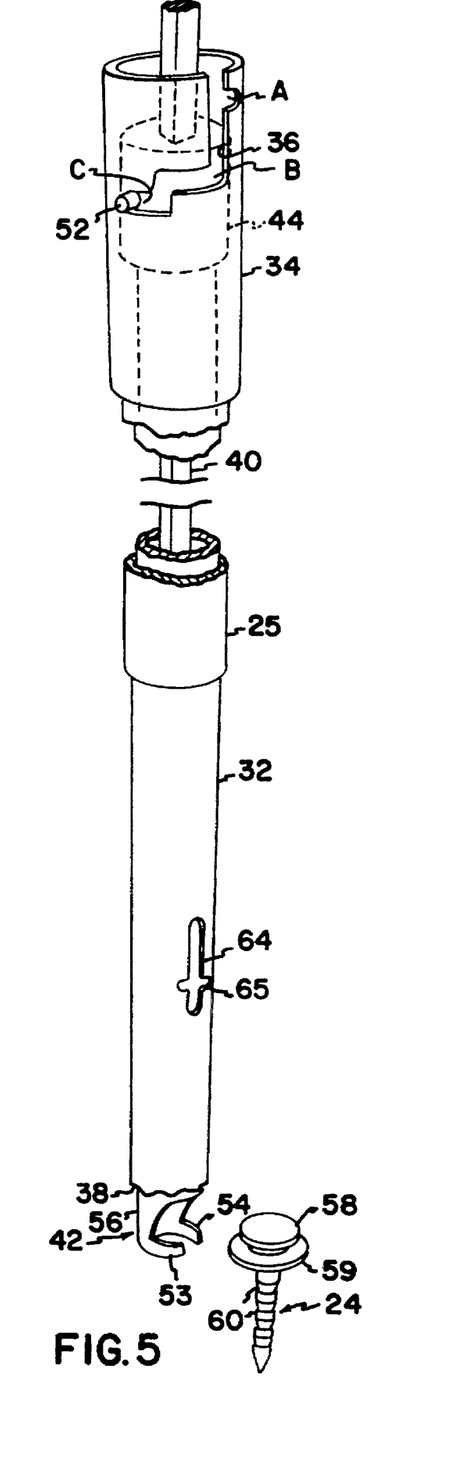
FIG. 5 is a perspective view, partially broken away of the instrument FIG. 3.
Figure 6:
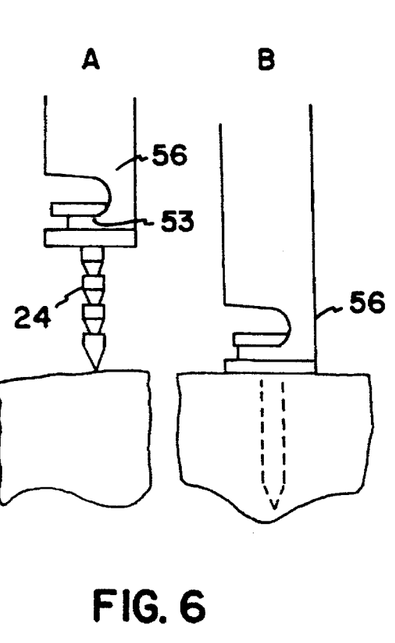
FIG. 6 is a fragmentary side view of a tack holder mechanism and tack, showing alternate positions, A and B, before and after embedment of a tack.
Figure 7:
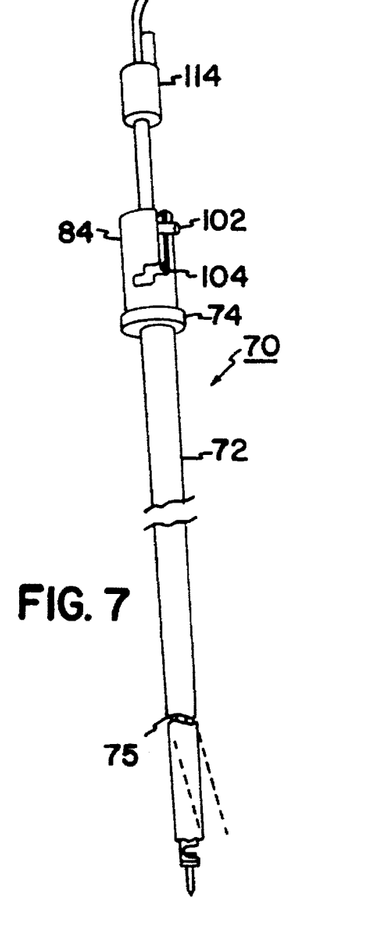
FIG. 7 is a perspective view of an alternate instrument in accordance with the invention, in which the distal end may be angulated for perpendicularity to a target surface.
Figure 8:
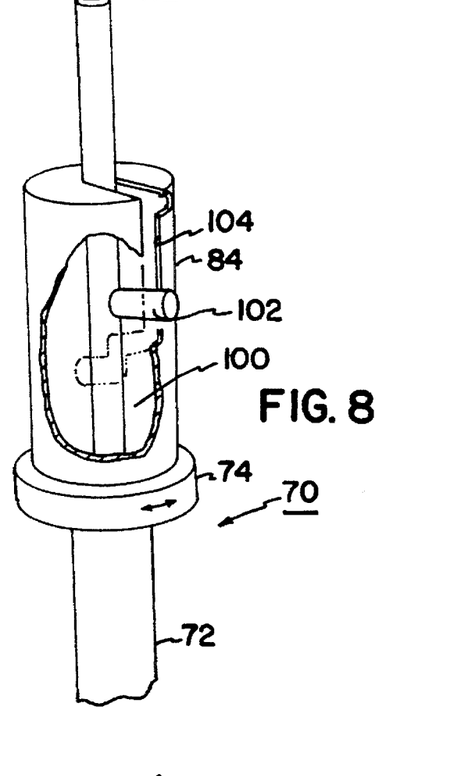
FIG. 8 is an enlarged perspective view, partially broken away, of the instrument of FIG. 7.

A long positioning and driving shaft 40 is disposed along the central axis of the sleeve 32, and extends to a tack retaining or holder mechanism 42 (see FIGS. 3 and 4 in particular) at the distal end. At its proximal end, the shaft 40 includes a positioning cylinder 44, best seen in FIG. 4, and extends outwardly through a positioning knob 46 to a threaded end 50. The positioning cylinder 44 is movable within the positioning sleeve 34 and includes a radially extending pin 52 that fits within the positioning slot 36, as best seen in FIG. 5.

In the tack holder mechanism 42, a pair of arms 53, 54 extend in opposite senses within a lateral plane normal to the central axis from an extension 56, to fit between spaced apart upper and lower heads 58, 59 on the surgical tack 24, which is typically of titanium. Serrations 60 along the shaft of the tack aid in retention of the tack 24, once embedded, but the force of retention may be overcome if it is desired to remove the tack 24. The extension 56 has a body diameter for a sliding fit within the sleeve 32 and the arms 53, 54 can also be withdrawn within the sleeve 32. Spaced apart from the arms 53, 54 on the tack holder mechanism 42 is a length of round tubing 62 fixed to the shaft 40, and providing a reference shoulder for a compression spring 63 which exerts a mechanical bias on the extension 56 and on a tack 24 retained between the arms 53, 54 to permit the tack to remain in position during withdrawal movements of the drive mechanism shaft 40 within the extension 56. The shoulders at the ends of the length of tubing 62 are positioned so that they align with the transverse arms 65 on a cruciform indicator window 64 in the sleeve 32, for different modes of operation. When the tack is fully retracted within the distal end of the sleeve 32, the distal end of the tubing segment 62 is aligned with the transverse arms 65 of the indicator window 64. However, when the proximal end of the tubing segment 62 is in alignment with the transverse arms 65, the tack 24 fully extends from the terminal edge 38 of the sleeve 32. A similar indicator window 64 may be disposed on the opposite side of the sleeve 32 if desired. Use of an indicator window for positive identification of tack position provides an added degree of assurance inasmuch as the tack 24 itself may be partially or wholly obscured by tissue.

At the proximal end of the shaft mechanism 40, the threaded portion 50 is detachably securable to a threaded slider 66 that is reciprocable over a short distance within a cylindrical weight 68, the slider 66 having a matching female thread to the male threaded end 50 of the shaft. By this means, the weight 68 when attached at the interior slider 66 may be accelerated freely through a short distance before impacting the proximal end of the shaft 40. This provides a smooth but forceful tapping action to embed the tack 24 in position, or alternatively to withdraw a secured tack that was previously embedded.

The operation of the instrument 20 shown in FIGS. 1 to 6 will be described independently of the surgical procedure that is used, although examples of abdominal rectopexy and prolapsed uterus provide typical illustrations of where the procedure is of greatest benefit. Briefly, the biocompatible mesh 22 is first inserted into the cavity in a tightly rolled condition, then unrolled, positioned, and tacked to the sacrum using the surgical tack 24, after which it is sutured or stapled to the organ to maintain the organ in position. For embedment of the tack 24, the instrument 20 is preferably introduced into the abdomen through a cannula 25 that is perpendicularly aligned with the sacral region at which embedment is to take place. During insertion, the tack 24 is fully withdrawn into the distal end 38 of the sleeve 32, by shifting the positioning pin 52 to the first position A (FIG. 5) in the positioning slot 36 using the knob 46. The serrated terminal edge 38 is engaged against the sacrum at the point of embedment and the shaft mechanism 40 is rotated until the pin 52 is in longitudinal alignment with the position B. The weight 66 is then attached to the proximal end of the shaft 40 and the shaft 40 is driven in by repeated tapping motions, until the point B is reached on the position slot 36. This corresponds to the full insertion position in FIG. 6. The position of full embedment of the tack 24 may be verified by a reference to the location of the proximal end of the tubing segment 62 to the transverse arms 65 within the window 64. To separate the tack 24 from the holder 42, the positioning pin 52 is moved to the position C, which moves the sleeve 32 back until the tack 24 is clear of the terminal edge 38. In this position also the arms 53, 54 are opposite the viewing window 64, so that a limited lateral movement of the distal end of the instrument 20 frees the arms 53, 54 from the space between the heads 58, 59 as depicted in FIG. 5. To remove a tack 24, the arms 53, 54 are inserted sideways between the double heads 58, 59 of the tack 24, and the weight 68 is impacted outwardly until separation of the tack is complete.

It will sometimes happen that the location of a tacking position within the body cavity is such, relative to the axis of entry of a cannula, that a tack cannot be embedded or extracted in a direction perpendicular to the surface of the sacrum. If the long axis of a tack that is interior to the body cavity can be shifted through an arc, however, this can remove the necessity for a separate penetration of the cavity wall with a cannula or trocar, and saves valuable time as well. The version of a laparoscopic tacker in accordance with the invention shown in FIGS. 7 to 10 accomplishes this result. In these Figures, the cannula 25 is not shown for purposes of more clearly seeing the device itself.

Figure 9:
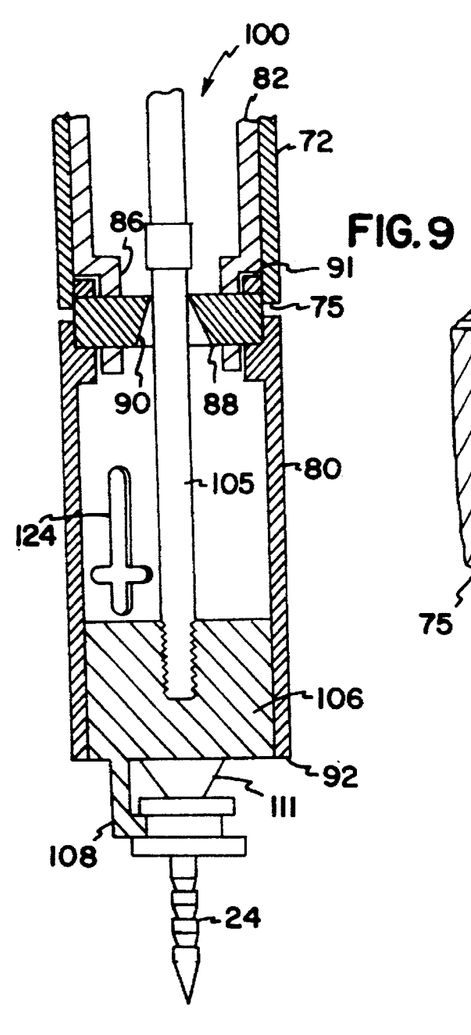
FIG. 9 is a side sectional view of the instrument of FIGS. 7 and 8, showing the angulation mechanism.
Figure 10:
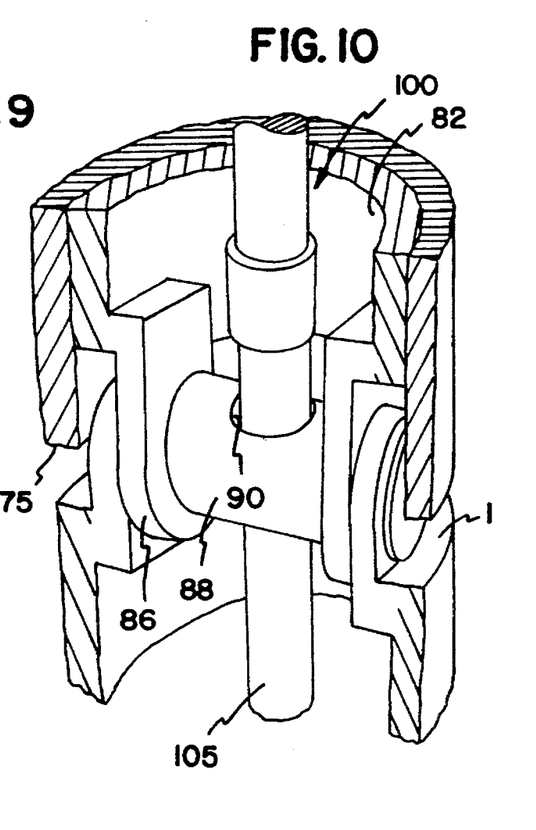
FIG. 10 is a fragmentary perspective view of a pivoting mechanism used in FIG. 9, showing further details thereof.

In the angulated laparoscopic tacker 70 FIGS. (7 to 10), a longitudinal cylinder body 72 is dimensioned to slide within a cannula (not shown), the cylinder body 72 being attached at its proximal end to a control ring 74 by which it may be rotated about its central axis. The peripheral edge of the distal end of the cylinder body 72 is configured to define a circumferential cam surface 75. The cam surface 75 is used in turning a pivotable end cylinder 80, which is nominally collinear with the cylinder body 72, and which has the same diameter, so that the end cylinder 80 defines an angulated tip or extension portion of the body 72. Within the cylinder body 72, an inner, concentric cylinder 82 is substantially co-extensive with the cylinder body 72 along the length of its central axis. At its proximal end the inner cylinder 82 is coupled to a fixed, hollow handle 84 for use by the surgeon in manipulating the device. At the distal end, along a plane transverse to the central axis of the cylinder body 72, as best seen in FIGS. 9 and 10, the inner cylinder 82 has a pair of depending bearing members 86 supporting a transverse pivot shaft 88 that defines a pivot axis for the end cylinder 80. A bore 90 in the pivot shaft 88 has two parallel sides and two converging sides (diverging in the proximal to distal direction) in separate quadrants about the central axis, for purposes described hereafter. The end cylinder 80 is suspended from the inner cylinder 82 by bearings 91, attached to the end cylinder 80 on each side of the pivot shaft 88. The bearings 91 are large enough to allow rotation of the end cylinder 80 about the pivot shaft 88 with a sliding fit. As described above in the example of FIGS. 1–6, the distal end of the end cylinder 80 has a terminal edge 92 of varying or serrated circumferential shape, so as to provide better engagement against a sacrum or other surface in which a tack is to be placed.

A central drive and positioning shaft mechanism 100 extends from the handle 84 down to the distal end of the end cylinder 82. Within the handle 84, the shaft mechanism 100 includes a transverse arm 102 that extends through a positioning slot 104 in the handle 84, which positioning slot 104 may have axial and circumferential segments defining successive operating positions as in the example in FIGS. 1–6. The shaft mechanism 100 extends down through the central axis of the inner cylinder 82, and through the bore 90 in the pivot shaft 88. A length 105 of the shaft mechanism, however, is a flexible shaft, such as a helically wound element which has sufficient rigidity along its length to permit driving force in either direction without buckling, even though it may be bent through a limited angle relative to the central axis. A tack holder body 106, slidable within the inner wall of the end cylinder 80, is engaged to the distal end of the shaft mechanism 100, and retains a tack holder device 108, having tack receiving arms, 109,110 as previously discussed. An elastomeric plug 111, between the tack holder body 106 and the tack 24, engages the top of the tack 24 to maintain it in positively secured position within the arms 109, 110. At the proximal end of the handle 84, the end of the shaft mechanism protrudes through to a threaded end 112 to which a pneumatic impeller 114 can be attached as desired.

Details of the pivot mechanism are best seen in FIG. 9, to which reference is now made. The cam surface 75 on the cylinder body 72 has a cam riser portion 75a circumferentially midway between the points of intersection of the pivot axis with the approximate end of the cylinder body 72. The proximal end of the end cylinder 80 similarly has a circumferential cam follower surface 122, so when the cam riser portion 75*a* engages a higher surface on the cam follower 122 on the end cylinder 80, during rotation of the cylinder body 72, the end cylinder 80 is pivoted or angulated through an angle. The flexible segment 105 of the shaft mechanism 100 curves within the mechanism, principally on the side within the end cylinder 80, accommodating the relative motion. The diverging surfaces on the bore 90 allow this bending to take place within adequate limits.

Figure 15:
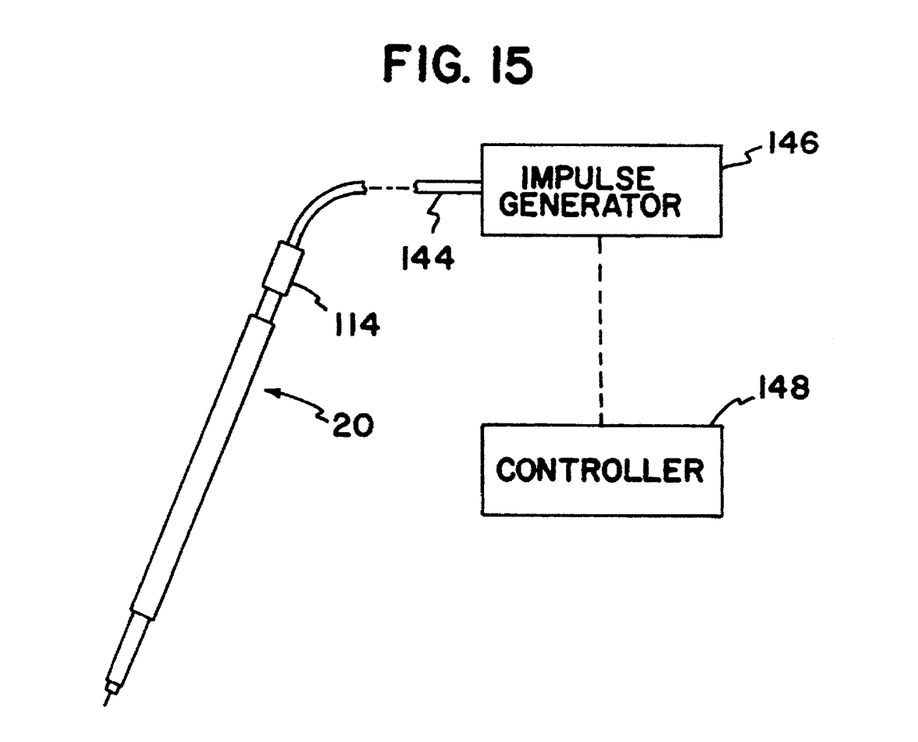
FIG. 15 is a schematic view of a control system for a pneumatic impeller, as shown in FIG. 7.
Figure 16:
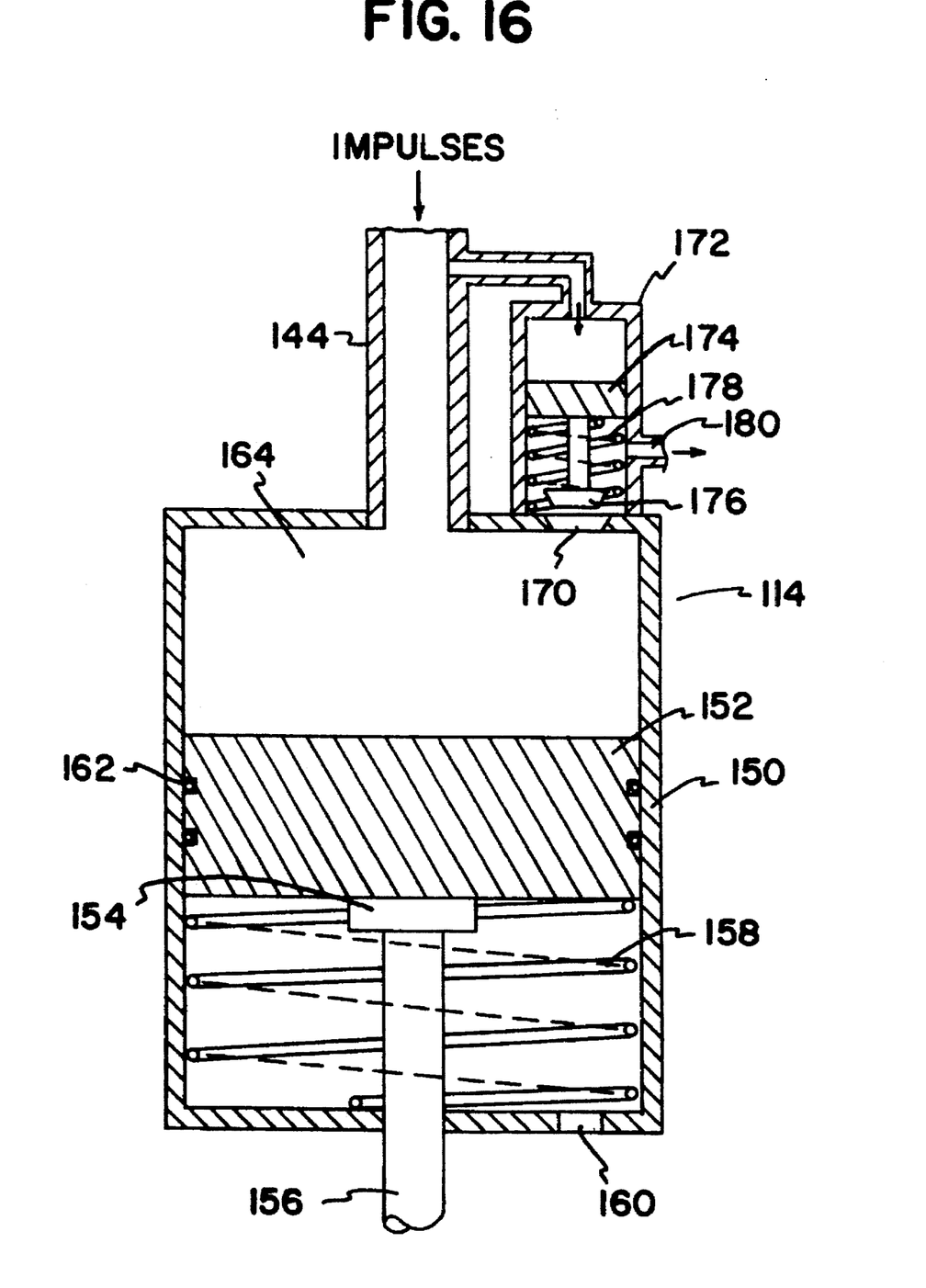
FIG. 16 is a side sectional view of a pneumatic impeller device.

The drive and positioning mechanism 100 can be reciprocated along its longitudinal axis, as by the use of a weighted mass or impeller 60 as described in conjunction with FIGS. 1–6. In this example, however a pneumatic impeller 114 as described below in conjunction with FIGS. 15 and 16 is attached and may be used in place of a positioning control knob. Different positions of the tack 24 relative to the terminal edge 92 of the end cylinder 80 can be set using the arm 102 in the handle 84 as previously described. The tack 24 thus can be held non-protruding concealed during entry, and extended in desired fashion beyond the distal end of the end cylinder 80 for embedment. Alternatively, the tack 24 may be removed by the reverse procedure. The end cylinder 80 includes, as in the prior example, a cruciform window 124 on one or both sides for visually verifying the tack position.

In the operation of this system of FIGS. 7 to 10, insertion is done as previously, with the tack 24 being concealed and protected within the end cylinder 80 as the cylinder body 72 is entered in the cannula (not shown). Thereafter, however, the proper angle of attack for entry of the tack 24 can be selected and the tack can be set at the proper angle by rotating the control ring 74 while viewing the angle of the end cylinder 80, until perpendicularity is achieved. Then the tack 24 can be extended by shifting the transverse arm 102 relative to the positioning slot 104. Thereafter the impeller 114 attached to the threaded end 112 of the shaft mechanism 100, can be actuated for driving the tack into position. A previously inserted tack which is to be removed, or a faultily inserted tack, can be removed by engagement of the arms 109, 110 into the space between the double heads of the tack 24, and undertaking the repeated tapping action in the reverse direction. For this purpose, however, a double acting pneumatic impeller or a reversed impeller is to be used.

Figure 11:
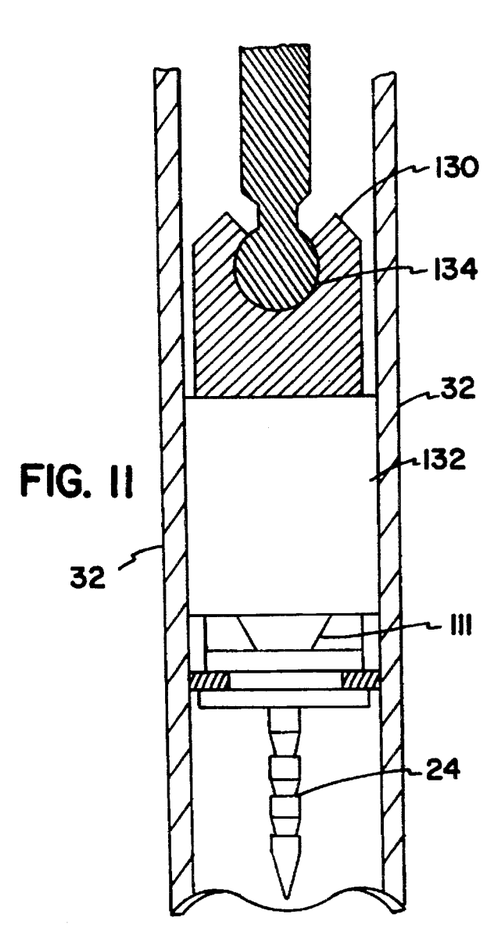
FIG. 11 is a simplified side view of a cartridge-type tack holder mechanism.
Figure 12:
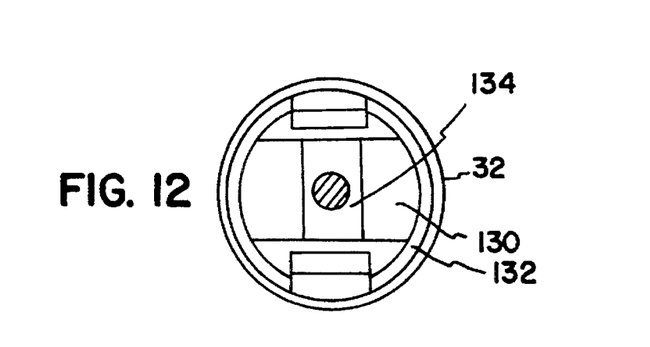
FIG. 12 is a top sectional view of the mechanism of FIG. 11.

Another useful feature that may be employed in either system is shown in FIGS. 11 and 12. In this example, in which only the terminal end fragment of a laparoscopic tacker is seen, the central positioning mechanism terminates in a ball 130, and the tack holder is in the form of a cartridge 132 having a fictionally engagable socket 134 which partially encircles the ball 130 at the end of the shaft. To insert a new tack for a given application, the laparoscopic tacker is removed, the prior cartridge is disengaged and a new cartridge, with pre-loaded tack attached, is substituted. This can be effected rapidly during a surgical procedure, so that several tacks can be embedded serially or tack sizes can be changed.

Figure 13:
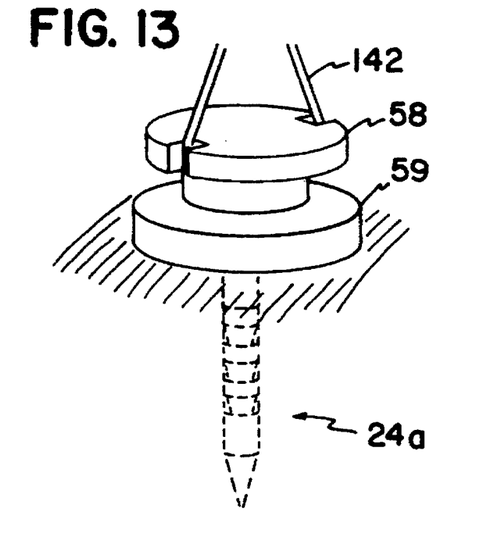
FIG. 13 is a perspective view of a tack with peripheral notches used for anchoring a suture filament.
Figure 14:
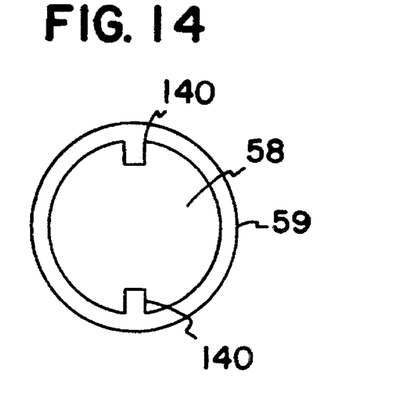
FIG. 14 is a top view of the tack of FIG. 13.

The embedded tack can serve other purposes in addition to attachment of an element to cartilage. Thus as seen in FIGS. 13 and 14, a tack 24*a* may have slots or notches 140 at diametrically opposed positions in the periphery of the b a upper head 58. A suture filament 142 may then be wrapped about half or the full circumference of the groove between the heads 58, 59 and taken out through the notches 140, so that the tack 24*a* serves as a temporary anchor or a permanent attachment point for the suture.

The pneumatic impeller 114 discussed in connection with the example of FIGS. 7–10 may be utilized as shown in FIG. 15 and constructed as seen in FIG. 16. With a compact, light weight impeller 114 attached to the instrument 20, only a pneumatic line 144 is added to the manipulated mass. This line 144 transports pneumatic impulses at a chosen periodicity from an impulse generator 146 (eg a reciprocating pump) which is activated by a controller 148, which is preferably remote, such as a fast pedal, or may be on the instrument 20 itself. If desired the pulses may be modulatable to deliver strokes of varying amplitude, frequency, or both.

An unidirectional pneumatic impeller 114 is depicted in FIG. 16, for use in embedment of a tack—if a pneumatic action is desired, then the arrangement must be double-ended or a complementary impeller operating in the reverse direction must be attached. For brevity, however, only the embedment direction is described since this is the mode that is typically employed.

The pneumatic impeller 114 comprises a cylinder chamber 150 within which a free piston 152 is engageable against the flat end 154 of a positioning and driving shaft 156 that extends through the instrument 20. A spring 158 within the chamber 150 biases the piston 152 in a direction away from the distal end, and a port 160 in this end of the chamber 150 prevents pressure buildup, although O ring seals 162 about the piston 152 prevent bypass. Pneumatic impulses are fed from the line 144 into a pressure compartment 164 within the chamber 150, overcoming the spring 158 compliance and impacting the piston 152 down against the flat end 154 of the shaft 156. By controlling the pressure differential end duration, the desired periodic tapping force is achieved. A relief post 170 in the wall of the pressure compartment 164 is closed as the impulse is received, by a bypass flow from the line 144 into a secondary chamber 172 containing a reciprocable small piston 174 to which a valve 176 is attached. A spring 178 normally holds the valve 176 open, allowing air to escape from the pressure compartment 164 via an exhaust port 180, when the larger piston 152 returns, so that reciprocation can take place without lessening the needed impact force for embedment.

Although a number of forms and variations have been described, it will be appreciated that the invention is not limited thereto but encompasses all modifications and expedients within the scope of the appended claims.

I claim:

1. A laparoscopic tack applicator instrument, comprising:

elongated cylindrical tube means for insertion through a laparoscopic port, the tube means having a central axis, a distal insertion end and an exterior proximal end;

central shaft means slidably disposed along the central axis, the shaft means including distal sacral tack holder means comprising a pair of lateral arms fixedly spaced apart between their terminal ends to define an open end and also including exterior positioning means for axial and rotational positioning of the shaft relative to the tube to determine the position of the open end of the arms so that the tack holder means may be disengaged from or engaged to a tack by a lateral motion.

2. A tack applicator instrument as set forth in claim 1 above, wherein the exterior positioning means includes an adjustable positioner at a predetermined spacing from the distal tack holder means and engaged to the cylindrical tube means, the adjustable positioner including a bi-coordinate positioning slot in the tube means for establishing predetermined axial and polar positions of the tack holder means.

3. A tack applicator instrument as set forth in claim 2 above, wherein the shape of the positioning slot in the tube means defines by axial and rotational variations an insertion position for concealing the tack in the tube means during insertion, a tack position for embedding or removing a tack, and an extended position for detaching or attaching a tack relative to the instrument.

4. A tack applicator instrument as set forth in claim 1 above, wherein the tube means is a principally linear element and includes a distal peripheral edge including contour variations from a plane transverse to the central axis for seating at a tack embedment area.

5. A tack applicator instrument as set forth in claim 1 above, wherein the tube means comprises means adjacent the distal end for varying the angle of the distal end relative to the central axis, and means at the proximal end of the tube means for controlling the means for varying the angle of the distal end wherein the tube means can be utilized to drive a tack into a sacrum.

6. A tack applicator instrument as set forth in claim 1 above, further including weighted impeller means removably coupled to the proximal end of the shaft means for imparting momentum thereto.

7. A tack applicator instrument as set forth in claim 1 above, wherein the instrument further comprises manual means coupled to the proximal exterior region of the shaft means for rotating the shaft means relative to the tube means.

8. A tack applicator instrument as set forth in claim 1 above, wherein the tube means includes a viewing window spaced proximally from the distal end thereof by a predetermined distance from the tack holder means such that the position of a tack relative to the tube means can be visualized.

9. A sacral tack applicator as set forth in claim 1 above, wherein the shaft means includes mechanical biasing means coupled to the holder means for securing the tack.

10. A device foe use in laparoscopic surgery, for embedding a tack in cartilage or bone, comprising the combination of:

elongated cylindrical tube means having a distal end for insertion in a body cavity through a surface penetration region, the tube means including a proximal end protruding from the body when inserted and means defining a viewing aperture spaced apart from the distal end and interior to the body when inserted;

tack retaining means disposed within the distal end region of the tube means;

positioning means disposed in the proximal region of the tube means and including shaft means extending through the tube means and coupled to the tack retaining means for positioning a tack therein relative to the distal end of the tube means, the positioning means including means visible through the viewing aperture indicative of the position of the tack retaining means relative to the end of the tube means; and impeller means attachable at the proximal end of the tube means and intercoupled via the shaft means to the tack retaining means, for embedding the tack.

11. The device as set forth in claim 10 above, wherein the tube means comprises a linear tube and the positioning means comprises a rigid shaft extending through the tube and tack holding means at the distal end of the shaft slidable within the tube.

12. The device as set forth in claim 11 above, wherein the tack holding means comprises a pair of arcuate arms lying substantially in a plane transverse to the tube axis, and the device further comprises a tack having a double head separated by a groove, the groove being sized to be received in the arms of the tack holding means.

13. A device as set forth in claim 12 above, wherein the positioning means comprises a hollow sleeve disposed concentrically about the axis of the tube in the proximal region thereof, and a positioning cylinder therewithin, wherein the hollow sleeve has a guide slot defining axial and rotational positions relative to the tube axis, and the positioning cylinder includes a radial position pin movable along the guide slot to different axial and rotational positions, thereby to change the position of the tack holding means and the tack relative to the distal end of the tube.

14. A device as set forth in claim 13 above, wherein the device further comprises weighted impeller means attachable to the proximal end of the shaft for adding a substantial mass to the shaft for driving a tack into position, the impeller means including slider means attachable to the shaft for free reciprocation of the weighted impeller means over a limited distance.

15. A device as set forth in claim 13 above, wherein the slot and position pin are configured to provide optional positions for the tack, wherein the tack is (1) concealed within the distal end of the tube for insertion, (2) aligned with the distal end of the tube for driving into embedded position, and (3) wherein the head end of the tack is free of the distal end of the tube for enabling disengagement of the tack from the tack holding means.

16. A device as set forth in claim 10 above, wherein the tube means includes a principal tube body and separate tube end means in the region of the distal end of the tube means for changing the angle of the tube end means, and wherein the positioning means includes means in the proximal region of the principal tube body for changing the angle of the tube end means relative to the longitudinal axis of the principal tube body.

17. The device as set forth in claim 16 above, wherein the means for changing the angle of the tube end means includes cam means between the principal tube body and the tube end means, and means coupled through the principal tube body for controlling the cam means from an exterior proximal region of the device, and wherein the shaft means includes a flexible section in the region of the cam means and the distal end of the tube end means, the flexible section having sufficient rigidity to impact driving forces.

18. A sacral tacker for use in laparoscopic surgery comprising:

an elongated cylindrical tube means for insertion through a laparoscopic port, the tube means having a central axis, an insertion end and a proximal exterior end;

a central shaft means disposed along the central axis within the tube means, the shaft means having a distal tack holder comprising a pair of lateral arms spaced apart between their terminal ends;

a tack having a shaft and a head attached thereto, the tack head having a circumferential groove thereabout for registration within the lateral arms of the tack holder;

said shaft means including a proximal positioning cylinder end at a predetermined spacing from the distal tack holder;

positioning sleeve means coupled to said tube means at the proximal exterior end thereof, said positioning sleeve means including a guide slot spaced from the distal end of the tube means by a predetermined distance such that control of tack position relative to the tube means can be established relative to the positioning cylinder position with respect to the guide slot.

19. A laparoscopic tacking device comprising:

a tube means having a length for extension through a cannula port into a body cavity in the region of a tacking site and an exterior portion at which an operator can manipulate a device extending through the tube means;

shaft means extending through the tube means, said shaft means including tack holder means at the distal end thereof, said tack holder means comprising means for laterally engaging a tack along a predetermined lateral direction and disengaging in the lateral direction opposite thereto, said shaft means further including bicoordinate shaft positioning means in the exterior portion thereof, the positioning means defining polar and axial positions for (1) tack concealment within the distal end of the tube means of a tack; (2) insertion of a tack; and (3) engagement and disengagement of a tack with respect to the tack holder means;

means associated with the portion of said tube means disposed within the body for viewing the position of the shaft means relative to the tube means; and impeller means engagable to the exterior portion of the shaft means for impacting the shaft means in the axial direction to drive a tack into position.

20. An instrument for implanting surgical tacks in cartilage during laparoscopic surgery comprising:

extended tube means having a first central axis and insertable into a body cavity, the tube means including an interior concentric tube within said tube means, said tube means being rotatable about the central axis relative to the interior tube, end tube means having a second central axis nominally collinear with the first central axis and coupled to the distal end of the interior tube, means disposed between the extended tube means and the end tube means for changing the angle of the end tube means central axis relative to the tube means central axis in response to rotation of the tube means;

shaft means extending through the tube means and end tube means, the shaft means including a distal tack holder means and a flexible section at least in the region between the tube means and end tube means wherein the flexible section is sufficiently rigid to avoid buckling during tack implementation.

21. An instrument as set forth in claim 20 above, wherein the means for changing the angle comprises cam means, wherein the coupling between the distal end of the interior tube and the end tube means comprises a transverse pivot shaft having a bore along the central axis and wherein the flexible section of the shaft means extends through the bore.

22. The method, for laparoscopic procedures, of positioning and inserting a sacral tack, having a tack shaft and a tack head, using an instrument having a elongated cylindrical tube and a central reciprocable shaft means wherein the shaft means has receiving arms on a distal end and guide means on an exterior end for positioning the shaft means in insertion, tack implantation, and tack disengagement positions, comprising the steps of:

sliding the head of the tack into the receiving arms of the reciprocable shaft means;

retracting the tack into the tube by moving the guide means into the insertion position;

inserting the instrument into a body cavity;

positioning the distal end of the tube at the desired tacking site;

placing the tack at the tack implantation position by positioning the guide means;

implanting the tack into the sacrum;

extending the tack outside the tube by moving the guide means to the disengagement position, and disengaging the sacral tacker from the tack.

23. A method as set forth in claim 22 above, wherein the step of implanting the tack into the sacrum further comprises the steps of:

attaching a weighted impeller onto the reciprocating shaft means;

moving the reciprocable shaft means by the guide means into the tack implantation position; and driving the impeller repetitively towards the tack until the tack is fully seated in the sacrum.

24. A method of positioning and removing a sacral tack, having a tack shaft and a tack head, using an applicator having a elongated cylindrical housing and a central reciprocating shaft, wherein the shaft has receiving arms on a distal end and a guide pin extending laterally from the shaft on a proximal end for positioning the shaft into insertion, control, and detachment positions in a guide slot disposed in the housing, comprising the steps of:

setting a guide pin into the detachment position;

sliding the receiving arms of the reciprocating plunger into a circumferential groove in the head of the tack;

rotating the housing to align the guide pin in the tack control position;

driving the impeller away from the insertion site thereby withdrawing the tack into the housing; and removing the sacral tack applicator from the laparoscopic port.

25. In a laparoscopic tacking instrument having a tack positioning and driving mechanism movable through a longitudinal hollow cylinder, the combination comprising:

coupling means coupled at the distal end of a positioning and driving mechanism for attachment of a tack holder device;

tack holder cartridge means slidable within a hollow cylinder and including means for releasably engaging to the coupling means, the tack holder cartridge means including means at the distal end thereof for engaging a tack to be driven, and means for retaining the tack against longitudinal movement.

26. A laparoscopic tack applicator instrument, comprising:

elongated cylindrical tube means for insertion through a laparoscopic port, the elongated cylindrical tube means having a central axis, a distal insertion end and an exterior proximal end; and central reciprocal shaft means slidably disposed along the central axis, the central reciprocal shaft means including distal sacral tack holder means comprising a pair of lateral arms spaced apart between their terminal ends and also including exterior positioning means for establishing predetermined positions of the shaft means relative to the distal end of the tube means for concealing the tack in the elongated cylindrical tube means, for embedding or removing a tack, and for detaching or attaching a tack, the exterior positioning means including means defining a bicoordinate positioning slot serving as physical reference for the predetermined positions of the shaft means.

27. A laparoscopic tack applicator instrument, comprising:

elongated cylindrical tube means for insertion through a laparoscopic port, the elongated cylindrical tube means having a central axis, a distal insertion end, a viewing window spaced from the tack holder means such that the position of a member relative to the tube means can be visualized, and an exterior proximal end; and central reciprocal shaft means slidably disposed along the central axis, the central reciprocal shaft means including distal sacral tack holder means comprising a pair of lateral arms spaced apart between their terminal ends, the shaft means including a reference surface spaced a known distance from the tack holder means and in position to be viewed through the viewing window, including positioning means exterior to the laparoscopic probe for axially and rotationally positioning the central reciprocal shaft means relative to the elongated cylindrical tube means.

28. A laparoscopic tack applicator instrument, comprising:

elongated cylindrical tube means for insertion through a laparoscopic port, the elongated cylindrical tube means having a central axis, a distal insertion end, and an exterior proximal end; and central reciprocal shaft means slidably disposed along the central axis, the central reciprocal shaft means including distal sacral tack holder means coupled to the distal end of the shaft means and impactable by the distal end thereof and comprising a pair of lateral arms spaced apart between their terminal ends; the shaft means also including exterior positioning means for axially and rotationally positioning the central reciprocal shaft means relative to the elongated cylindrical tube means, the shaft means also including mechanical biasing means coupled between the shaft means and the tack holder means for securing a tack in position between the arms of the tack holder means.

* * * * *